(12) United States Patent
Askill

(10) Patent No.: US 6,521,221 B2
(45) Date of Patent: Feb. 18, 2003

(54) METHODS AND COMPOSITIONS TO ENABLE THE SAFE AND EFFECTIVE HARVESTING OF TISSUES AND ORGANS

(75) Inventor: Ian N. Askill, Colorado Springs, CO (US)

(73) Assignee: Flowers Park Ltd., Winsford (GB)

( * ) Notice: Subject to any disclaimer, the term of this patent is extended or adjusted under 35 U.S.C. 154(b) by 0 days.

(21) Appl. No.: 10/010,181

(22) Filed: Nov. 6, 2001

(65) Prior Publication Data

US 2002/0068266 A1 Jun. 6, 2002

Related U.S. Application Data

(60) Provisional application No. 60/246,177, filed on Nov. 6, 2000.

(51) Int. Cl.[7] .................................................. A01N 1/00
(52) U.S. Cl. .......................................................... 424/75
(58) Field of Search ........................................... 424/75

(56) References Cited

U.S. PATENT DOCUMENTS

| | | | |
|---|---|---|---|
| 3,654,239 A | * 4/1972 | McIntire et al. | 526/193 |
| 5,254,132 A | * 10/1993 | Barley et al. | 606/214 |
| 5,306,490 A | 4/1994 | Barley | |
| 5,403,591 A | 4/1995 | Tighe et al. | |
| 5,580,565 A | * 12/1996 | Tighe et al. | 424/400 |
| 5,653,769 A | 8/1997 | Barley et al. | |
| 5,807,563 A | * 9/1998 | Askill et al. | 424/402 |

FOREIGN PATENT DOCUMENTS

| | | |
|---|---|---|
| WO | WO 93/25196 | 12/1993 |

\* cited by examiner

Primary Examiner—Michael G. Hartley
Assistant Examiner—Konata M. George
(74) Attorney, Agent, or Firm—Burns, Doane, Swecker & Mathis L.L.P.

(57) ABSTRACT

Disclosed are methods and compositions capable of rapidly preparing mammalian tissue and organs for harvesting and subsequent transplantation while minimizing the potential for infection of the harvested tissues and organs. This invention is also directed to methods and compositions used to prepare the donor for subsequent handling by a mortician.

16 Claims, No Drawings

METHODS AND COMPOSITIONS TO ENABLE THE SAFE AND EFFECTIVE HARVESTING OF TISSUES AND ORGANS

CROSS-REFERENCE TO RELATED APPLICATIONS

This application claims the benefit of U.S. Provisional Patent Application Ser. No. 60/246,177 filed Nov. 6, 2000 which application is incorporated herein by reference in its entirety.

BACKGROUND OF THE INVENTION

1. Field of the Invention

This invention is directed to methods and compositions capable of rapidly preparing mammalian tissue and organs for harvesting and subsequent transplantation while minimizing the potential for infection of the harvested tissues and organs. This invention is also directed to methods and compositions used to prepare the donor for subsequent handling by a mortician.

2. References

The following publications, patent applications and patents are cited in this application as superscript numbers:

[1] Barley, "*Methods for Retarding Blister Formation by Use of Cyanoacrylate Adhesives*", U.S. Pat. No. 5,306,490, issued Apr. 26, 1994.

[2] Barley, et al., *Methods for Treating Suturable Wounds by Use of Sutures and Cyanoacrylate Adhesives*, U.S. Pat. No. 5,254,132, issued Oct. 19, 1993

[3] McIntire, et al., *Process for the Preparation of Poly (α-Cyanoacrylates)*, U.S. Pat. No. 3,654,239, issued Apr. 4, 1972

[4] Barley, et al., International Patent Application Publication No. WO 93/25196, for *Methods for Treating Non-Suturable Wounds by Use of Cyanoacrylate Adhesives*, published Dec. 23, 1993

[5] Barley, et al., *Methods for Reducing Skin Irritation From Artificial Devices by Use of Cyanoacrylate Adhesives*, U.S. Pat. No. 5,653,769, issued Aug. 5, 1997

[6] Tighe, et al., *Methods for Inhibiting Skin Ulceration by Use of Cyanoacrylate Adhesives*, U.S. Pat. No. 5,403,591, issued Apr. 4, 1995

[7] Tighe, et al., for *Use of Cyanoacrylates for Providing a Protective Barrier Film for the Skin*, U.S. Pat. No. 5,580,565, issued Dec. 6, 1996

[8] Askill, et al., for *Methods for Draping Surgical Incision Sites*, U.S. Pat. No. 5,807,563 issued Sep. 15, 1998

All of the above publications, patent applications and patents are herein incorporated by reference in their entirety to the same extent as if each individual publication, patent application or patent was specifically and individually indicated to be incorporated by reference in its entirety.

State of the Art

The procedures for harvesting tissues and organs for transplantation, implantation, research and other medical uses are fraught with complications which can cause reluctance to approve the use of the deceased in a donor program and limit the utility of the recovered tissues. Among these complications are infection of the removed tissues as well as ensuring that the donor's body is cosmetically acceptable after removal of the desired tissues and/or organs.

The infection rate for harvested tissues is approximately 30% despite extensive anti-infective procedures during organ and/or tissue harvest. After treatment of the harvested tissues and organs, there are approximately 10% that remain unusable due to infection.

Current practice in human cadavers is to first prepare the skin for subsequent tissue and/or organ harvesting by use of alcohol washes, followed by iodophor scrubs such as Betadine, followed by draping the incision site with a surgical incise drape such as Ioban. Such procedures are time consuming and expensive and all of the preparations have to be removed and all incisions have to be repaired to make the donor cosmetically presentable to family and friends.

Sutures and staples are frequently used for incision closures in human cadavers, but without the hemostasis mechanisms present in living tissue, mechanical closure will not prevent egress of body fluids. Commercial superglues, such as ethyl cyanoacrylate, are sometimes used to seal these incisions but the resulting polymer is too brittle and can easily crack whereas the reactive monomer can react too quickly making it hard to control. These superglues also have an unpleasant sharp odor and are respiratory irritants.

This invention is directed, in part, to the discovery that the in situ formation of a cyanoacrylate polymeric film at the site of tissue and/or organ harvesting overcomes many of the prior art problems noted above. For example, the cyanoacrylate polymer is known in the art to have bacteriostatic properties and the cyanoacrylate monomer permits the inclusion of compatible antimicrobial agents if such is desired. Still another advantage is the formation of an appropriately configured film which completely covers the transplantation area and forms a waterproof film over the skin, thereby inhibiting infection. Subsequent to tissue and/or organ harvesting, the reformation of the polymeric film over the incision site prevents fluid loss as well as improves the cosmetic appearance of the donor. Finally, the use of suitable cyanoacrylates with or without an appropriate perfume overcomes prior art problems with unpleasant odors and respiratory irritants.

The use of cyanoacrylate polymers per this invention is in contrast to their known medical uses as an alternative or adjunct to sutures[2] or as a hemostat[3]. Other described uses of cyanoacrylate prepolymers include their use on mammalian tissue to form polymeric films which are utilized:

to prevent friction blister formation[1], in treating small non-suturable wounds[4], in inhibiting surface skin irritation arising from friction between the skin surface and artificial devices such as tapes, prosthetic devices, casts, etc.[5], as surgical incise drapes[8], in inhibiting skin ulcerations[6], and forming a protective film to inhibit skin degradation due to incontinence.[7]

SUMMARY OF THE INVENTION

This invention is directed to methods for the rapid and effective preparation of donor skin for tissue and/or organ transplation by the in situ formation of a cyanoacrylate film from a cyanoacrylate prepolymer. A film-forming cyanoacrylate prepolymer can also be used to seal incisions and tissue/organ harvest sites so as to restore mechanical integrity and prevent fluid leakage from these sites. Preferably, the cyanoacrylate prepolymer compositions contain an antimicrobial agent or a plurality of agents to further inhibit infection in the harvested tissue and/or organs.

Such methods involve application of a cyanoacrylate prepolymer composition onto the cadaver skin at the site of tissue and/or organ transplantation followed by in situ polymerization of the prepolymer to form a polymeric film. The cyanoacrylate prepolymer composition can be applied as a liquid/gel to the skin surface and can include antimicrobial agents, and the like. Subsequent to formation of the cyanoacrylate film, an incision is made there through and the appropriate tissues/organs are harvested. In a particularly preferred embodiment, a cyanoacrylate prepolymer is then used to seal incisions and tissue/organ harvest sites so as to restore mechanical integrity to the cadaver and/or to prevent fluid leakage from these sites.

Accordingly, in one of its method aspects, this invention is directed to a method for harvesting tissue and/or organs from a mammalian cadaver which method comprises:

(a) identifying the tissue and/or organ to be harvested from a mammalian cadaver;

(b) applying a sufficient amount of a composition comprising a polymerizable cyanoacrylate ester to the skin covering the tissue and/or organ defined in (a) above so as to cover this skin with the composition;

(c) polymerizing the cyanoacrylate ester so as to form a flexible, waterproof, adhesive polymer film which adheres to and overlays the skin area(s) where the composition was applied; and (d) harvesting said tissue and/or organ by incision through the polymeric film and the underlying skin and subsequent removal of the tissue and/or organ.

Preferably, the polymerizable cyanoacrylate ester comprises an ester which, in monomeric form, is represented by formula I:

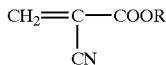

where R is selected from the group consisting of:
alkyl of 3 to 10 carbon atoms,
alkenyl of 2 to 10 carbon atoms,
cycloalkyl groups of from 5 to 8 carbon atoms,
phenyl,
2-ethoxyethyl,
3-methoxybutyl,
3-propoxypropyl,
and a substituent of the formula:

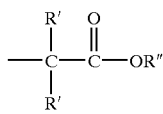

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 2 to 8 carbon atoms. Even more preferably, R is butyl, pentyl or octyl and most preferably, R is n-butyl.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

Preferably, the mammalian cadaver is a human cadaver.

More preferably, subsequent to harvesting of the tissue and/or organ, the incision site and/or tissue/organ harvest sites are sealed by application of a cyanoacrylate prepolymer so as to restore mechanical integrity to the cadaver and/or to prevent fluid leakage from these sites.

DETAILED DESCRIPTION OF THE PREFERRED EMBODIMENTS

This invention is directed to methods of rapidly preparing mammalian tissue and organs for harvesting and subsequent transplantation while minimizing the potential for infection of the harvested tissues and organs.

Definitions

As used herein, the following terms have the following meanings:

The term "mammalian cadaver" refers to the bodily remains of a mammalian subject for which tissue and/or organs will be harvested. Preferably, the mammalian cadaver is a human cadaver.

The term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 3 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl or R is an alkoxyalkyl of from 4 to 10 carbon atoms such as ethoxyethyl or propoxypropyl. More preferably, R is butyl, pentyl or octyl and most preferably, R is n-butyl. Mixtures of such compounds can also be employed as disclosed by Berger, et al., U.S. Pat. No. 5,998,472 which is incorporated herein by reference in its entirety.

A preferred cyanoacrylate ester for use in the invention is 2-ethoxyethyl cyanoacrylate.

Such polymerizable cyanoacrylate esters are sometimes referred to herein as prepolymers and compositions comprising such esters are sometimes referred to herein as prepolymer compositions.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "biocompatible plasticizer" refers to any material which is soluble or dispersible in the cyanoacrylate composition, which increases the flexibility of the resulting polymeric film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and $C_2$–$C_4$-acyl tri-n-hexyl citrates.

The term "antimicrobial agent" refers to agents which destroy microbes (i.e., bacteria, fungi, yeasts and viruses) thereby preventing their development and their pathogenic action.

Suitable antimicrobial agents for use in this invention include, for example, poloxamer iodophors, hexyl resourcinol, salicyclic acid, 2-phenyl-ethanol, 4-chloro-3,5-dimethylphenol, benzoic acid, sorbic acid and the like.

Methods

The methods of this invention comprise the in situ formation of a cyanoacrylate polymer film on the skin surface at the site of incision of the mammalian cadaver where tissue and/or organ harvesting is to occur which polymeric film acts as a barrier film in inhibiting the introduction of or migration of pathogens into the incision site.

The treatment protocol preferably involves skin preparation prior to in situ formation of the cyanoacrylate polymer film at the incision site. Specifically, this site is conventionally pretreated by cleaning with an appropriate antimicrobial composition. The site is then preferably dried, e.g., blotted dry, and then an adherent polymeric film is formed over this site by application of a polymerizable cyanoacrylate composition. As noted above, this composition comprises polymerizable cyanoacrylate monomers and/or reactive oligomers which, upon contact with the skin site polymerizes in situ to form a polymeric film.

Polymerization occurs at ambient conditions for a sufficient period of time to allow polymerization to proceed. In general, the particular length of time required for polymerization will vary depending on factors such as the amount of adhesive composition applied, the temperature of the site, the moisture content of the site, the extent surface area of the site, and the like. However, in a preferred embodiment, polymerization is generally complete within about 10 to about 60 seconds while the site is maintained at or below ambient conditions (e.g., from about 0° C. to about 20° C.); however, in some cases, polymerization can occur up to about 5 minutes. During this period, the cadaver is maintained in a position which permits the cyanoacrylate to polymerize and form a polymeric film while minimizing any movement which might dislodge the cyanoacrylate from that site or create undesirable bonding.

Sufficient amounts of the composition are employed to cover (i.e., coat) the entire site with a layer of the cyanoacrylate polymer. If necessary, excess cyanoacrylate monomer and/or oligomer can be removed with a wipe or tissue paper before polymerization or, after polymerization, any polymer formed at unintended sites can be removed with materials such as acetone.

After polymerization, the resulting polymeric film forms a barrier film which strongly adheres to the skin, is flexible and waterproof. Such strong adherence effectively eliminates the possibility that the film will separate from the cadaver which would otherwise permit the undesirable introduction of microbes and/or permit leakage from the harvested site.

The polymeric film should be maintained in an unbroken manner over the entire site. This can be assured by careful application of the cyanoacrylate adhesive onto the site. Additionally, the use of a plasticizer will facilitate the maintenance of the polymeric film in an unbroken manner and will inhibit cracking of the film.

In one embodiment, after application of the initial polymeric layer, a second, preferably thinner, layer is applied thereto. Additional amounts of cyanoacrylate adhesive composition can be applied as needed to maintain an unbroken coating covering the site.

Application is conducted under conditions wherein the polymeric film preferably has a thickness of no more than about 1 millimeter and, more preferably, the polymer layer has a thickness of from about 2 to about 500 microns and still more preferably from about 20 to about 100 microns. If thinner polymeric films are desired, then the polymeric film should have a thickness of from about 2 to about 50 microns and preferably from 10 to 40 microns. The amount of cyanoacrylate composition applied to a unit area to obtain such thicknesses is well within the skill of the art.

The size and thickness of the polymeric film formed onto the site can be readily controlled by the amount and viscosity of cyanoacrylate adhesive composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate composition and the like.

In applicators, the cyanoacrylate composition is stored at ambient conditions and can be provided in sterile form.

In a preferred embodiment, the prepolymeric cyanoacrylate composition is presented in a telescopic applicator with a foil-sealed rear compartment containing, e.g., 6 grams, of this composition. The compartment is made from polypropylene and is heat-sealed at the end with a laminated aluminum/polyethylene foil. The remainder of the housing is made from high-density polyethylene, has a piercing device close to the front, and has a heat-bonded, small-pore polyurethane sponge attached to the front to spread the liquid.

To apply the composition, the applicator is held with the sponge pointing upward and the rear pressed against a sterile surface. This forces the rear, telescoping compartment onto the piercing device, which pierces the foil seal and releases the cyanoacrylate composition. The applicator is then inverted and the solution now soaks the sponge. The sponge is applied onto the incision site on the mammalian cadaver to apply a uniform coating of composition which, in situ, forms a polymeric film at this site.

In a particularly preferred embodiment, an applicator known as a "popule" manufactured by Hardwood Products Company, LLC of Gilford, Me., USA is utilized.

Subsequent to polymer film formation, an incision is made at the site to excise the to-be-harvested tissue and/or organ. The harvesting procedure then occurs under conventional procedures well known in the art.

After harvesting is completed, the incision site and/or tissue/organ harvest sites are sealed by application of a prepolymeric cyanoacrylate composition so as to restore mechanical integrity to the cadaver and/or to prevent fluid leakage from these sites. In one embodiment, the prepolymeric cyanoacrylate composition used to seal the incision and/or harvest sites is the same as that used to form the polymeric film over the skin prior to incision. However, such is not necessary. For example, sealing of the incision site does not require use of a cyanoacrylate composition comprising an antimicrobial agent since the desired tissue and/or organ have been removed.

Compositions

The cyanoacrylate compositions comprising the polymerizable cyanoacrylate esters are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin application. Contrarily, where application is to be made to a specific position on the skin, higher viscosity compositions, including those containing thixotropic materials, are preferred to prevent "running" of the compositions to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate ester employed in these compositions is almost entirely in monomeric form and the composition has a viscosity of from about 2 to about 100 centipoise at 20° C.

A thickening agent is optionally employed to increase the viscosity of the composition, which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239 and 4,038,345 both of which are incorporated herein by reference in their entirety.

The cyanoacrylate adhesive compositions may include a plasticizer and such plasticizers are included in the composition from about 10 to 30 weight percent and more preferably from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition during storage. In a particularly preferred embodiment, this inhibitor is sulfur dioxide which is employed at from about 50 to 500 ppm, preferably 50 to 200 ppm, based on the total weight of the composition absent any antimicrobial agent. Other preferred polymerization inhibitors include glacial acetic acid, free radical inhibitors (e.g., hydroquinones) and the like which can be used alone or in combination with $SO_2$.

The polymerizable cyanoacrylate ester compositions may additionally contain one or more optional additives such as medicaments, colorants, perfumes, anti-diffusion agents, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. Medicaments are added as necessary to achieve an antiseptic environment. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of a compatible antimicrobial agent as disclosed, for example, in U.S. Pat. No. 5,684,042, which is incorporated by reference in its entirety. Such compositions preferably comprise from about 1 to about 40 and preferably 5 to 30 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use. Suitable such compositions are disclosed in U.S. patent application Ser. Nos. 08/913,681 which discloses compositions of cyanoacrylate/povidone-iodine complexes and 09/215,078 which discloses compositions of cyanoacrylate esters/iodine complexes of polyoxyalkylene polymers. Both applications are incorporated herein by reference in their entirety.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, preferably from about 5 to about 40 weight percent and more preferably from about 10 to 25 weight percent is added to the cyanoacrylate composition based on the total weight of the composition.

Other suitable antimicrobial agents include complexes of iodine molecules with poloxamers or copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The use of a compatible antimicrobial agent in the composition permits the agent to be released from the polymeric film thereby reducing microbial growth under the film.

One particularly preferred prepolymeric cyanoacrylate composition comprises ethoxyethyl cyanoacrylate containing about 0.5 weight percent 2-bromo-2-nitro-1,3-propanediol, 500 ppm hydroquinone and 100 ppm sulfur dioxide all based on the total weight of the composition.

Utility

The methods described herein are useful in forming a polymeric film over the site of incision during organ and/or tissue harvesting in a mammalian cadaver. The polymeric film finds particular utility in inhibiting microbial contamination at this site so as to reduce the incidence of infection in the harvested tissue and/or organ. Such mammalian cadavers preferably include human cadavers as well as animal cadavers suitable for xenotransplation such as pigs. The maintenance of the polymeric film over this site is expected to reduce the incidence of infection by inhibiting microbial contamination at this site.

In addition, the methods of this invention permit subsequent to harvesting of the tissue and/or organ, the sealing of the incision site and/or tissue/organ harvest sites by a prepolymeric cyanoacrylate composition so as to restore the mechanical integrity to the cadaver and/or to prevent fluid leakage from these sites.

The following examples illustrate certain embodiments of the invention but is not meant to limit the scope of the claims in any way.

Examples 1–2 below illustrate how the methods of this invention could be practiced. In these examples, the following abbreviations have the definitions set forth below. Unless defined, the terms have their generally accepted meanings. In addition, unless otherwise stated, all percentages are weight percentages based on the total weight of the composition.

g=gram
mL=milliliter
ppm=parts per million

EXAMPLE 1

A 45-year-old organ donor, victim of a lethal head injury, is prepared for organ harvest by coating the entire torso with a cyanoacrylate-film-forming composition comprising ethoxyethyl cyanoacrylate containing 0.5% 2-bromo-2-nitro-1,3-propanediol, 500 ppm hydroquinone, and 100 ppm sulfur dioxide. 50 mL of the composition is contained in a polyethylene bottle with a screw cap and a foil seal. The cap is removed and an applicator head is screwed onto the bottle. The applicator head contains a piercing device to breach the foil, and a sponge for applying the fluid. About 40 mL of the formulation is needed to thinly cover the skin, and dries within 45 seconds to form a flexible antimicrobial film. An incision is made through this film and the kidneys are harvested. Following the excision, the wound is closed using a small amount of the remains of the antimicrobial formulation. This is accomplished by unscrewing the applicator head, dipping a small disposable pipette into the residual liquid and extracting about 0.5 mL of the formulation. The pipette is used to spread this liquid over the inside edges of the incision, which is then held firmly closed for 60 seconds in which time the tissue becomes firmly bonded by the adhesive. Once the incision is closed, the sponge applicator is re-installed on the bottle, which is used to apply a final sealing coat of film-forming adhesive over the incision. This sets within 60 seconds to form a thin, flexible adhesive sealing film.

EXAMPLE 2

A young male gunshot victim has the skin from his back and thighs harvested using a dermatome. The harvest sites are extensive and weep fluid. These sites are sealed with an application of 30% butyl cyanoacrylate, 70% octyl cyanoacrylate containing 500 ppm hydroquinone and 100 ppm sulfur dioxide, tinted to skin tone with mixed iron and titanium oxides. The pigments and cyanoacrylate formulation are mixed prior to use and then applied using a special applicator. The applicator comprises a tube, closed at one end, which contains 15 mL of the formulation. This mixing is prevented from leaking by a crushable glass ampoule that is a tight "press fit" halfway up the tube and beyond which is a mixing chamber. The ampoule contains 2 g of a skin tone pigment blended from titanium dioxide and mixed iron oxides. Beyond the mixing chamber is an angled flange to which is attached a polyurethane sponge that covers the open end of the tube.

A pair of levers is formed into the outside of the applicator tube adjacent to the enclosed ampoule. The film-forming composition is released by squeezing the levers, which causes the applicator tube to deform, and breaks the ampoule. The applicator is then shaken to mix the two components, which are then applied to the required area with the sponge. The reactive film-forming composition sets on the exposed tissue within 60 seconds and acts as a sealant for the tissue while also hiding the underlying structures.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A method for harvesting tissue and/or organs from a mammalian cadaver which method comprises:
    (a) identifying the tissue and/or organ to be harvested from a mammalian cadaver;
    (b) applying a sufficient amount of a first composition comprising a polymerizable cyanoacrylate ester to the skin covering the tissue and/or organ defined in (a) above so as to cover this skin with the composition;
    (c) polymerizing the cyanoacrylate ester so as to form a flexible, waterproof, adhesive polymer film which adheres to and overlays the skin area(s) where the composition was applied; and
    (d) harvesting said tissue and/or organ by incision through the polymeric film and the underlying skin and subsequent removal of the tissue and/or organ.

2. The method according to claim 1 wherein said first polymerizable cyanoacrylate ester composition comprises a cyanoacrylate ester, which in monomeric form, is represented by formula I:

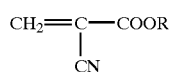

where R is selected from the group consisting of:
    alkyl of 3 to 10 carbon atoms,
    alkenyl of 2 to 10 carbon atoms,
    cycloalkyl groups of from 5 to 8 carbon atoms,
    phenyl, 2-ethoxyethyl,
3-methoxybutyl,
3-propoxypropyl,
and a substituent of the formula:

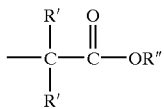

wherein each R' is independently selected from the group consisting of:
  hydrogen and methyl, and
R" is selected from the group consisting of:
  alkyl of from 1 to 6 carbon atoms,
  alkenyl of from 2 to 6 carbon atoms,
  alkynyl of from 2 to 6 carbon atoms,
  cycloalkyl of from 3 to 8 carbon atoms,
  aralkyl selected from the group consisting of benzyl, methylbenzyl and phenylethyl,
  phenyl, and
  phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 3 to 10 carbon atoms.

4. The method according to claim 3 wherein R is alkyl of from 3 to 8 carbon atoms.

5. The method according to claim 1 wherein R is selected from the group consisting of butyl, pentyl, octyl or 2-ethoxyethyl.

6. The method according to claim 5 wherein R is n-butyl or 2-ethoxyethyl.

7. The method according to claim 1 wherein said first cyanoacrylate adhesive composition further comprises an antimicrobially effective amount of a compatible antimicrobial agent.

8. The method according to claim 7 wherein the compatible antimicrobial agent is a poloxmer iodine complex.

9. The method according to claim 1 wherein said first cyanoacrylate adhesive composition further comprises a biocompatible plasticizer.

10. The method according to claim 9 wherein said biocompatible plasticizer is dioctyl phthalate.

11. The method according to claim 1 wherein said first cyanoacrylate adhesive composition further comprises a polymerization inhibitor.

12. The method according to claim 11 wherein said polymerization inhibitor is selected from $SO_2$, hydroquinone and mixtures thereof.

13. The method according to claim 1 wherein said mammalian cadaver is a human cadaver.

14. The method according to claim 1 wherein subsequent to procedure d), the incision site and/or tissue/organ harvest site is sealed by application of a sufficient amount of a second composition comprising a polymerizable cyanoacrylate ester to the skin the incision site and polymerizing the cyanoacrylate ester.

15. The method according to claim 14 wherein the second composition is identical to said first composition.

16. The method according to claim 14 wherein the second composition is different from said first composition.

* * * * *